United States Patent
Cho et al.

(10) Patent No.: US 7,432,111 B2
(45) Date of Patent: Oct. 7, 2008

(54) NON-CONTINUOUS IMMUNOASSAY DEVICE AND IMMUNOASSAY METHOD USING THE SAME

(75) Inventors: Young-Shik Cho, Kyonggi-do (KR); Hyo-Keun Lee, Kyonggi-do (KR); Byung-Ki Cho, Kyonggi-do (KR)

(73) Assignee: Standard Diagnostics, Inc. (KR)

( * ) Notice: Subject to any disclaimer, the term of this patent is extended or adjusted under 35 U.S.C. 154(b) by 265 days.

(21) Appl. No.: 11/191,543

(22) Filed: Jul. 28, 2005

(65) Prior Publication Data
US 2006/0172435 A1    Aug. 3, 2006

(30) Foreign Application Priority Data
Feb. 2, 2005    (KR) .................. 10-2005-0009677
Apr. 15, 2005    (KR) .................. 10-2005-0031525

(51) Int. Cl.
*G01N 33/53*    (2006.01)

(52) U.S. Cl. ............ 436/514; 435/287.1; 435/287.2; 435/287.7; 435/287.9; 436/169; 436/518; 436/530; 436/805; 436/810; 436/815

(58) Field of Classification Search ............ 435/287.1, 435/287.2, 287.7, 287.9; 436/169, 514, 518, 436/530, 805, 810, 815
See application file for complete search history.

(56) References Cited

U.S. PATENT DOCUMENTS

| | | | | |
|---|---|---|---|---|
| 5,712,170 A | * | 1/1998 | Kouvonen et al. | 436/518 |
| 5,948,695 A | * | 9/1999 | Douglas et al. | 436/518 |
| 6,046,057 A | * | 4/2000 | Nazareth et al. | 436/514 |
| 6,162,639 A | * | 12/2000 | Douglas | 435/287.1 |
| 6,271,045 B1 | * | 8/2001 | Douglas et al. | 436/518 |
| 6,297,020 B1 | * | 10/2001 | Brock | 435/7.1 |
| 2002/0192835 A1 | | 12/2002 | Cho et al. | 436/170 |

FOREIGN PATENT DOCUMENTS

EP    0 762 123    3/1997

(Continued)

OTHER PUBLICATIONS

International Search Report; Nov. 4, 2005; 3 pages.

(Continued)

*Primary Examiner*—Bao-Thuy L Nguyen
(74) *Attorney, Agent, or Firm*—St. Onge Steward Johnston & Reens LLC

(57) ABSTRACT

A non-continuous immunoassay device which includes two or more separated pads for immunoassay analysis, and is capable of controlling the migration speed of a mobile phase between the separated pads, and an immunoassay method using the same are disclosed. The immunoassay device includes a first pad receiving a mobile phase; a second pad which is spatially separated from the first pad by a predetermined distance, and to which the mobile phase migrates; an upper case for covering the upper parts of the first pad and the second pad; a lower case for covering the lower parts of the first pad and the second pad; and a connecting member which is formed on at least one of the upper case and the lower case, and located between the first pad and the second pad to form a passage for moving the liquid sample.

13 Claims, 13 Drawing Sheets

FOREIGN PATENT DOCUMENTS

| | | |
|---|---|---|
| JP | 9072904 A | 3/1997 |
| JP | 10511774 A | 11/1998 |
| JP | 2001513884 A | 9/2001 |
| JP | 2002040026 A | 2/2002 |
| JP | 2003194818 A | 7/2003 |
| WO | 9635123 A1 | 11/1996 |
| WO | WO 98/37416 | 8/1998 |

OTHER PUBLICATIONS

Japanese Office Action, Feb. 20, 2008, 5 pages.

* cited by examiner

Fig. 10
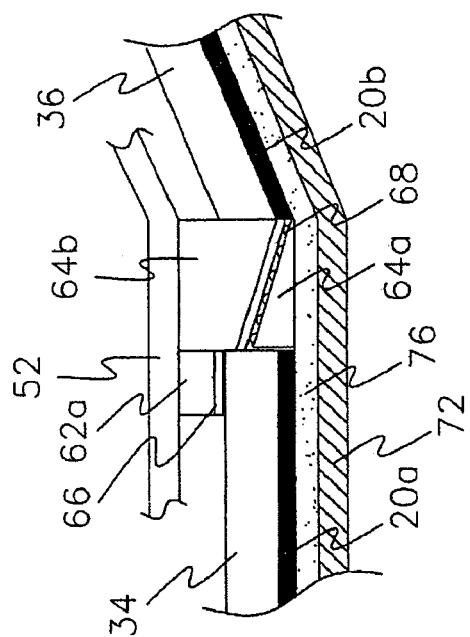
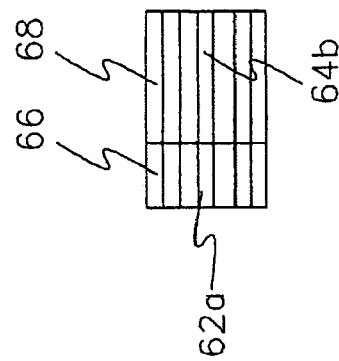
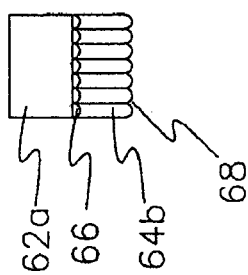

NON-CONTINUOUS IMMUNOASSAY DEVICE AND IMMUNOASSAY METHOD USING THE SAME

This application claims priority of Korean Patent Application Nos. 2005-9677 filed on Feb. 2, 2005 and 2005-31525 filed on Apr. 15, 2005.

FIELD OF THE INVENTION

This invention relates to a non-continuous immunoassay device. More particularly, this invention relates to a non-continuous immunoassay device which includes two or more separated pads for immunoassay analysis, and is capable of controlling the migration speed of a mobile phase between the separated pads, and an immunoassay method using the same.

BACKGROUND OF THE INVENTION

The immunochromatographic assay known as a "rapid testing method" has been developed for a simple, qualitative and quantitative analysis of a small amount of analyte. The assay utilizes antigen-antibody reaction for analysis, and is applied in various fields or industries, such as a medical field for diagnosing diseases, agriculture, livestock raising, foods, military, environment and so on. Typically, the immunochromatographic assay is carried out with an assay strip, or with an assay device which comprises a plastic case and the assay strip installed in the case. FIG. 1 is a cross-sectional view of the conventional assay strip for immunochromatographic assay. As shown in the FIG. 1, the conventional assay strip 10 includes a sample pad 12 for receiving a liquid sample, a conjugate pad 14 containing a conjugate, a porous membrane pad 16 immobilized with a binder (antibody or antigen) 16a which specifically combines with an analyte in the sample and/or the conjugate, and an absorbent pad 18 for finally receiving the liquid sample. The conjugate is produced by conjugating a label which generates a signal detectable by a naked eye or a sensor to a ligand such as an antigen or an antibody. These pads are consecutively arranged on a plastic backing 20, and the connecting ends of the neighboring pads are overlapped by a predetermined distance. In case the assay strip 10 is installed in a plastic case to form the assay device, a sample receiving hole for introducing a sample to the sample pad 12, and a result observation window for observing the test result are formed on the upper portion of the case.

In the immunochromatographic assay using the assay strip 10, a liquid sample is injected into the sample pad 12. The injected liquid sample flows along the conjugate pad 14 and the porous membrane pad 16 by a capillary action, and is finally absorbed by the absorbent pad 18. In this case, the conjugate in the conjugate pad 14 also migrates along with the liquid sample. If a target analyte exists in the sample, the conjugate is bound to the binder 16a which is immobilized on the porous membrane pad 16 via the target analyte (i.e., the target analyte intervenes between the conjugate and the binder 16a. "sandwich reaction"), or the conjugate and the target analyte are competitively bound to the binder 16a ("competition reaction"). Therefore, the existence of the analyte can be determined by detecting the conjugate bound to the binder 16a with a naked eye or a sensor. However, in order to control the flow rate of the mobile phase, such as the liquid sample, the pore size of the porous membrane pad 16 should be modified. Thus, the flow speed of the liquid sample and the reaction rate of antigen-antibody reaction cannot be effectively controlled with the conventional assay strip 10.

Namely, the dilution of the liquid sample with a diluent, and/or the antigen-antibody reaction(s) between the binder 16a, the analyte in the liquid sample and/or the conjugate cannot be carried out for enough time interval, which deteriorates the sensitivity and specificity of the immunochromatographic assay. In addition, when a pad, for example the porous membrane pad 16, is damaged during the production of the assay strip 10, the whole assay strip 10 should be discarded because the pads are serially connected. The conventional assay strip 10 has a further disadvantage in that the shape of the assay strip 10 or the shape of the assay device including the strip 10 is limited to the straight rod shape.

In addition, when whole blood is used as the liquid sample, the flow speeds of the whole blood components, such as the hemolyzed erythrocyte, are relatively slow compared to the analyte in the liquid sample. Namely, the whole blood components, such as the hemolyzed erythrocyte, pass through the sample pad 12 and the conjugate pad 14 having pores of small sizes with relatively slow speed, and remain in the porous membrane pad 16 for a long time. Therefore, when the desired antigen-antibody reaction is carried out on the detection line on which the binder 16a is immobilized, the whole blood components still exist on the porous membrane pad 16, namely, on the background, and the color of the detection line is covered with the red color of the whole blood components. This makes it difficult to determine the test result. Therefore, the test result should be determined after the whole blood components completely pass the detection line. However, this is not practical since it takes much time for the detection or determination of the test result. Such problems mainly occur when using the whole blood to examine disease, such as malaria, AIDS, hepatitis C, hepatitis B, syphilis, helicobacter pylori, tumor markers (AFP, PSA, CEA), tuberculosis, SARS, Dengue fever, leprosy, and so on.

SUMMARY OF THE INVENTION

Therefore, it is an object of the present invention to provide an immunoassay device for controlling the flow speeds of liquid buffer, a conjugate, an analyte and so on, and having superior sensitivity and specificity in immunochromatographic assay.

It is other object of the present invention to provide an immunoassay device which is capable of controlling the migration speed of a mobile phase flowing through the pads for immunoassay.

It is another object of the present invention to provide an immunoassay device which is capable of controlling the antigen-antibody reaction time according to the kind of the antigen-antibody reaction.

It is still another object of the present invention to provide a non-continuous immunoassay device and an immunoassay method using the same, in which the pads for the device can be produced in a simple manner, and it is not necessary to discard whole pads when a pad is damaged during the production.

It is yet still another object of the present invention to provide a non-continuous immunoassay device and an immunoassay method using the same, in which the shape of the device can be modified for easy applying the sample and for easy detection of the test result.

It is yet still another object of the present invention to provide a non-continuous immunoassay device and an immunoassay method using the same, in which the detection of the test result is easy, and the background of the detection line is clear even when whole blood is used as the liquid sample.

BRIEF DESCRIPTION OF DRAWINGS

A more complete appreciation of the invention, and many of the attendant advantages thereof, will be readily apparent as the same becomes better understood by reference to the following detailed description when considered in conjunction with the accompanying drawings, wherein:

FIG. 10 shows a front view (A), a bottom view (B) and a left side view (C) of a connecting member of the non-continuous immunoassay device according to the fourth embodiment of the present invention;

DETAILED DESCRIPTION OF PREFERRED EMBODIMENTS

Figure 1:
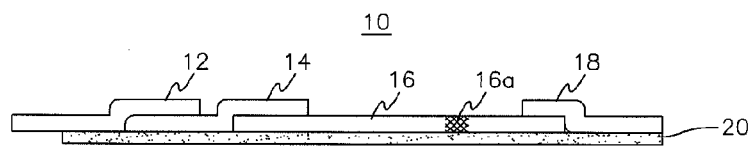
FIG. 1 is a cross-sectional view of a conventional assay strip.

Preferred embodiments of this invention will be explained in detail with reference to the accompanying drawings. In the following detailed description, same reference numeral is used to denote same or similar component.

Figure 2:
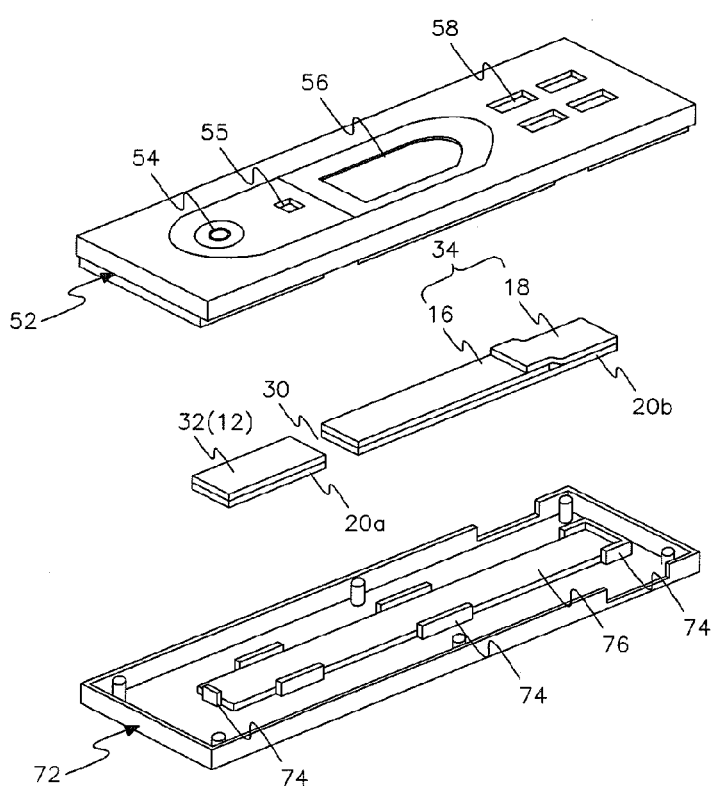
FIG. 2 is an exploded perspective view of a non-continuous immunoassay device according to the first embodiment of the present invention.
Figure 3:
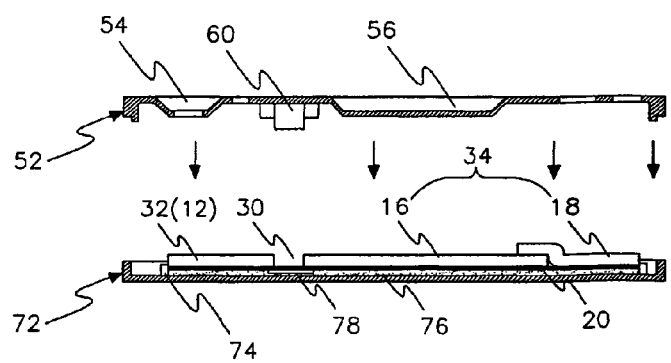
FIG. 3 is a side cross-sectional view of a non-continuous immunoassay device according to the first embodiment of the present invention.

FIGS. 2 and 3 are an exploded perspective view and a side cross-sectional view, respectively, of a non-continuous immunoassay device according to the first embodiment of the present invention. As shown in FIGS. 2 and 3, the immunoassay device according to the first embodiment of the present invention includes the first pad area 32 and the second pad area 34 which are spatially separated from each other by a predetermined distance. The upper and the lower parts of the first and second pad areas 32, 34 are partially or completely covered with an upper case 52 and a lower case 72, respectively. The first and the second pad areas 32, 34 can be fixed on the lower case 72 by being inserted between a plurality of guides 74 formed on the lower case 72, or can be fixed in grooves (not shown) formed on the upper or lower case 52, 72. Preferably, a pad-supporting member 76 can be formed on the lower case 72 for supporting the first and the second pad areas 32, 34. The pad-supporting member 76 can be made of a plate shaped shock-absorbing plastics. As shown in FIG. 3, a connecting member 60 is formed on the upper case 52 so that the connecting member 60 is located in the space 30 between the first pad area 32 and the second pad area 34 when the upper case 52 and the lower case 72 are assembled. The connecting member 60 can be a protrusion which is separated from the lower case 72 or the optional pad-supporting member 76 by a predetermined distance when the upper case 52 and the lower case 72 are assembled. The liquid sample applied to the first pad area 32 migrates to the second pad area 34 through the gap between the connecting member 60 and the lower case 72 or between the connecting member 60 and the pad-supporting member 76 by a capillary action. Therefore, the connecting member 60 produces capillary passage (gap) for migrating the liquid sample in the space 30 between the first pad area 32 and the second pad area 34. The connecting member 60 can be a liquid non-permeable protrusion extending from the upper case 52, and if necessary, can be formed on the lower case 72 or formed on both of the upper case 52 and the lower case 72 to produce a gap therebetween.

In the immunoassay device according to the present invention, the first pad area 32 and the second pad area 34 may include (i) a sample pad 12 for receiving a liquid sample that are expected to contain a target analyte and/or a diluent for diluting the liquid sample, (ii) a conjugate pad containing a conjugate, which is produced by conjugating a label (for example, gold particles, colored polystyrene micro particles, enzyme, fluorescent dye, conductive polymer, magnetic particles) which generates a signal detectable by a naked eye or a sensor to a ligand (for example, an antigen or an antibody) which can bind with the analyte, (iii) an optional auxiliary pad containing a material for facilitating the antigen-antibody reaction or for suppressing a nonspecific reaction when whole blood is used as the liquid sample, (iv) a porous membrane pad 16, on which at least one detection line (test line) is formed by immobilizing a binder (antibody or antigen) which can be specifically bonded with the analyte in the sample and/or with the conjugate, (v) an absorbent pad 18 for finally absorbing the liquid sample, and so on. The term "pad area" refers to one or more pads, and maybe used to refer to one pad alone or two or more pads together.

In the first embodiment of the present invention, the first pad area 32 includes at least the sample pad 12 for receiving the liquid sample, and the second pad area 34 includes one or more pads to which the liquid sample migrates. For example, as shown in FIG. 2, the first pad area 32 includes the sample pad 12, and the second pad area 34 includes the porous membrane pad 16 and the absorbent pad 18 which overlaps at their connecting ends. Alternatively, the first pad area 32 may include two or more pads, which either overlaps at their connecting ends or are separated from each other, and the examples of the two or more pads include (i) the sample pad 12 and a conjugate pad, (ii) the sample pad 12 for whole blood, an auxiliary pad, and a conjugate pad, and so on. The second pad area 34 can include other necessary immunoassay pads. The auxiliary pad can contain a material for facilitating an antigen-antibody reaction or for suppressing a nonspecific reaction when whole blood is used as the sample. For example, the auxiliary pad can contain a reagent which is necessary for analysis but hemolyzes red blood cell(s) (RBC) when mixed with whole blood sample. By applying such reagent on the auxiliary pad, hemolysis of RBC can be prevented, and migration of the hemolyzed RBC to the porous membrane pad 16 can be prevented. In detail, the auxiliary pad can be installed between the sample pad 12 and the conjugate pad so that the material contained in the auxiliary pad can be mixed with the liquid sample from which RBC is filtered and removed by the sample pad 12. The porous membrane pad 16 can be made of a porous material, such as nitrocellulose, glass fiber, polyethersulfone (PES), cellulose, nylon, and so on, and preferably can be made of nitrocellulose having the pore size of about 5 μm to about 15 μm. The first pad 32 and the second pad area 34 can be formed on the upper portions of two separate plastic backings 20*a*, 20*b*, respectively. By using the plastic backings 20*a*, 20*b*, the first pad area 32 and the second pad area 34 can be produced more conveniently and can be easily mounted on the lower case 72. The plastic backings 20*a*, 20*b* can be made of a material such as polypropylene film, polyester film, polycarbonate film, acrylic film, or so on, and can be preferably made of polypropylene film.

Figure 4:
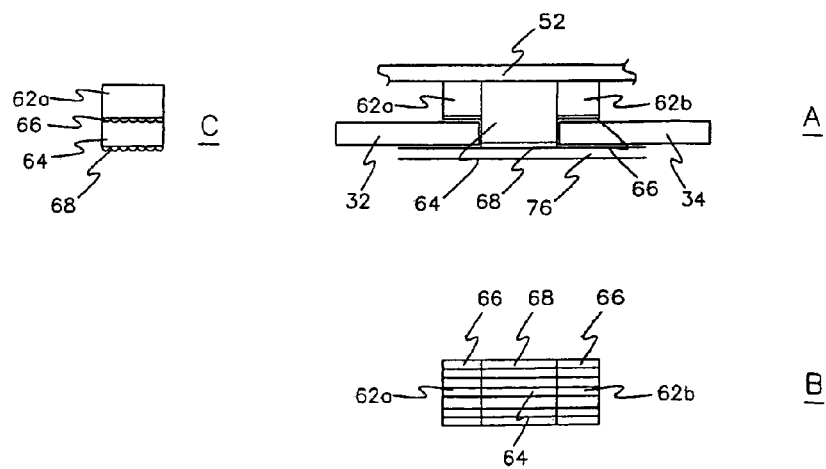
FIG. 4 shows a front view (A), a bottom view (B) and a side view (C) of a connecting member of the non-continuous immunoassay device according to the first embodiment of the present invention.

FIG. 4 shows a front view (A), a bottom view (B) and a side view (C) of the connecting member 60 which is formed on the upper case 52 and/or the lower case 72. As shown in FIG. 4, the connecting member 60 can be a protrusion 64 having shoulders 62*a*, 62*b* which are formed to the directions of the first pad 32 and the second pad area 34, respectively. The shoulders 62*a*, 62*b* compress and fix the end of the first pad area 32 and the end of the second pad area 34, respectively, and the protrusion 64 forms the capillary passage between the first pad area 32 and the second pad area 34. Therefore, it is preferable that the protrusion 64 is firmly inserted into the space 30 between the first pad area 32 and the second pad area 34. It is also preferable that a plurality of micro-protrusions 66 is formed on the shoulder 62*a*, 64*b* for firm and complete fixing of the first and the second pad areas 32, 34. It is also preferable that a plurality of micro-protrusions 68 is formed on the protrusion 64 for forming a regular capillary passage by maintaining the gap distance between the protrusion 64 and the pad-supporting member 76 constantly. By forming the micro-protrusion 68 on the protrusion 64, the capillary passage can be formed around the micro-protrusion 68 even though the micro-protrusion 68 contacts with the pad-supporting member 76. The micro-protrusion 66, 68 may be a straight line shaped protrusion formed along the direction of the migration of the liquid sample as shown in FIG. 4, but not limited thereto, and can be semi-spherical shaped protrusions, hexahedron shaped protrusions, and so on. The gap distance between the connecting member 60, specifically, the protrusion 64 and the lower case 72 or the pad-supporting member 76 can be adjusted by changing the heights of the protrusion 64 and micro-protrusion 68. By adjusting the gap distance, the migration speed of the mobile phase such as liquid sample passing through the connecting member 60 can be controlled. Therefore, the antigen-antibody reaction rate can also be controlled.

In the present invention, the distance between the first pad area 32 and the second pad area 34 and the gap distance of the capillary passage formed between the upper case 52 and the lower case 72 can be properly determined according to the kind of antigen-antibody reaction and/or the kind of sample. For example, the distance between the first pad area 32 and the second pad area 34 is from about 0.5 mm to about 5 mm, preferably from about 1 mm to about 3 mm, and more preferably about 2 mm, and the gap distance of the capillary passage can be from 0.005 to 1 mm, preferably from 0.01 to 0.5 mm, and more preferably from 0.01 to 0.2 mm. When the distances are more than the above defined ranges or less than the above defined ranges, the migration of the mobile phase, such as the liquid sample, may not be properly carried out.

The connecting member 60 can be treated with hydrophobic or hydrophilic materials to control the antigen-antibody reaction rate. Generally, it is difficult for aqueous solution to pass a hydrophobic region. When a compound in the aqueous solution is bind to the hydrophobic region, the hydrophobic region is likely to be changed to a hydrophilic region, and then aqueous solution can pass more easily the hydrophilic region. Therefore, if the connecting member 60 is treated with hydrophobic or hydrophilic materials, the migration speed of a mobile phase which migrates from the first pad area 32 to the second pad area 34 can be controlled. When the connecting member 60 is treated to reduce the migration speed, the first pad area 32 works as a reaction chamber for holding the reaction mixture for a predetermined time. The methods of treating the connecting member 60 includes the method of coating the connecting member 60 with hydrophobic or hydrophilic latex particles or compounds, the method of adhering hydrophobic or hydrophilic group on the connecting member 60 by using a plasma, and so on. Exemplary hydrophobic latex particles include polymer such as polystyrene, polypropylene, polyethylene, polyester, and so on. Exemplary hydrophilic latex particles include polymer having hydrophilic group such as carboxyl, amine, and hydroxyl group on its surface. Useful hydrophobic compound includes ink and a long chain fatty acid such as palmitic acid, stearic acid, or oleic acid, and useful hydrophilic compound includes hydrophilic polymer such as surfactant, glycerol, and polyvinyl alcohol. For introducing the hydrophilic group such as a carboxylic group or an amine group to the connecting member 60 by using a plasma treatment, a hydrophilic monomer such as acrylic monomer, methacrylic monomer, unsaturated amide, diene monomer, triene monomer or so on can be plasma-graft-polymerized on the surface of the connecting member 60, or oxygen or nitrogen can be treated with a hydrogen plasma on the connecting member 60. For introducing the hydrophobic group to the connecting member 60 by using a plasma treatment, hexafluoropropene ($CF_2$=$CF$—$CF_3$) can be plasma polymerized on the surface of the connecting member 60 to produce a thin layer having C—F linkage.

Referring again to FIG. 2, a sample receiving hole 55 is formed on the upper case 52 at the position corresponding to the sample pad 12, and an observation window 56 is formed on the upper case 52 at the position corresponding to the detection line or zone of the porous membrane pad 16. Also, a diluent receiving hole 54 can be formed at the position corresponding to the end portion of the sample pad 12, and an air ventilation hole 58 can be formed at the position corresponding to the absorbent pad 18. By applying a diluent for diluting a liquid sample through the diluent receiving hole 54, a test deviation can decrease, and the specificity and sensitivity of analysis can increase. The air ventilation hole 58 is provided for air-ventilation at the absorbent pad 18, and prevents the liquid sample in the absorbent pad 18 from flowing backward to the direction of the observation window 56. Therefore, background clearance of the test result can be induced, and the result of immunoassay can be observed more clearly. The air ventilation hole 58 can be formed at the lateral position of the absorbent pad 18, or can be formed at both of upper and lateral positions of the absorbent pad 18. If necessary, a plurality of guides and protrusions can be formed on the upper case 52 and the lower case 72 for disposing, fixating, or compressing the immunoassay pads appropriately. The upper case 52 and the lower case 72 can be assembled by typical connecting means such as connecting grooves and protrusions. Alternatively, the upper case 52 and the lower case 72 can be provided as an integrated form, namely, as a single body.

In operation of the immunoassay device in accordance with the first embodiment of the present invention, a liquid sample is applied to the first pad area 32, i.e., sample pad 12 through the sample receiving hole 55 of the upper case 52. The applied sample migrate through the capillary passage formed by the connecting member 60 to the second pad area 34 consisting of the porous membrane pad 16 and the absorbent pad 18. Because the gap distance of the capillary passage is adjusted according to the analyte in the sample, the conjugate, and the antigen-antibody reaction, the antigen-antibody reaction(s) can be carried out for desired time interval at each pad. Therefore, the connecting member 60 works as a reaction barrier inducing a flow delay of the mobile phase, or works as an antigen-antibody reaction rate controller. The liquid sample and/or the conjugate that migrate to the porous membrane pad 16 react with a binder immobilized on the porous membrane pad 16, and generate a signal detectable by naked eyes or a sensor.

Figure 5:
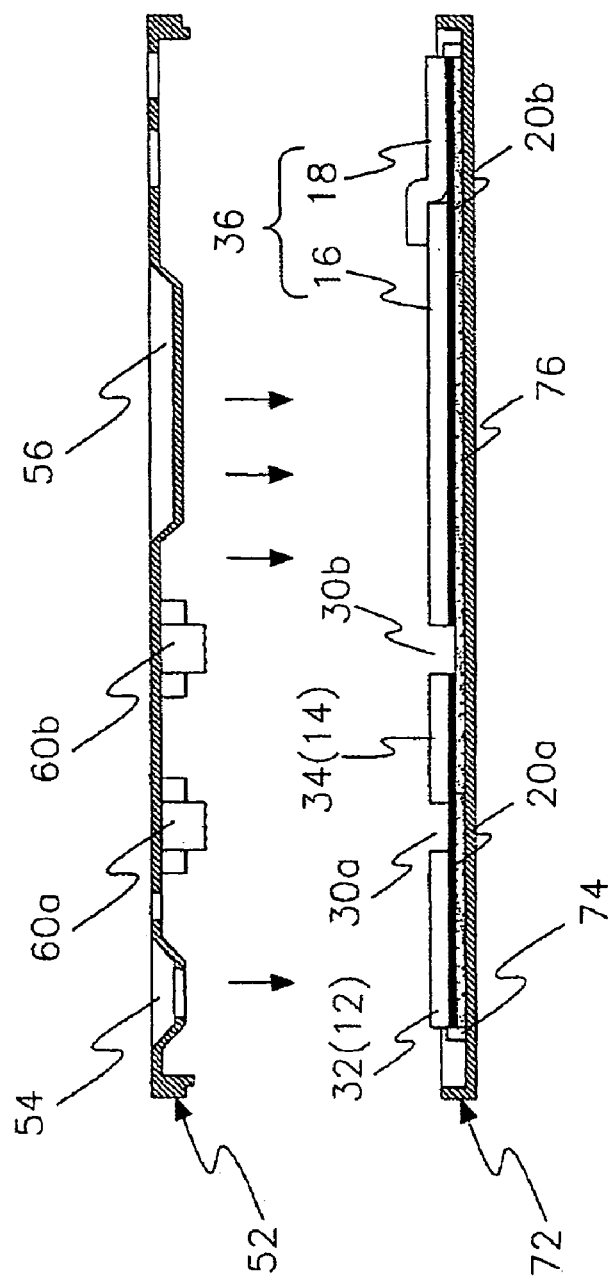
FIG. 5 is a side cross-sectional view of a non-continuous immunoassay device according to the second embodiment of the present invention.

FIG. 5 is a side cross-sectional view of a non-continuous immunoassay device according to the second embodiment of the present invention. The immunoassay device of this embodiment has substantially same configuration with that of the first embodiment except that the first, the second and the third pads 32, 34, 36 are separated by predetermined distances, and consecutively formed on the two plastic backings 20a, 20b, and the first connecting member 60a is located at the space 30a between the first pad area 32 and the second pad area 34, and the second connecting member 60b is located at the space 30b between the second pad area 34 and the third pad area 36. In the second embodiment, the first pad area 32 includes a sample pad 12, the second pad area 34 includes a conjugate pad 14 or an auxiliary pad, and the third pad area 36 includes a porous membrane pad 16 and an absorbent pad 18 which are overlapped at their connecting ends. The first pad area 32 and the second pad area 34 are formed on the first plastic backing 20a, and the third pad area 36 is formed on the second plastic backing 20b. Similarly, three pads, for example, a sample pad 12, an auxiliary pad, and a conjugate pad 14, which are separated by predetermined distances, can be formed on the first plastic backing 20a, and a porous membrane pad 16 can be formed on the second plastic backing 20b. The four pads can be connected with total three connecting members.

When two or more connecting members 60a, 60b are used, the migration rate of the mobile phase passing each pad can be controlled individually, which increases the sensitivity of immunoassay more effectively. In addition, when a pad is damaged, only the damaged pad can be exchanged instead of discarding whole pads. When the conjugate pad 14 is used and the immunoassay is carried out by the sandwich type reaction, the liquid sample applied to the sample pad 12 migrates to the conjugate pad 14 by capillary action and the analyte in the sample and the ligand of the conjugate produce an immune complex by an immunologic reaction. The immune complex then migrates to the porous membrane pad 16 along with the sample flow, and is captured at the detection zone (test line) where a binder is immobilized, through an immunologic specific binding. When the conjugate pad 14 is used and the immunoassay is carried out by the competitive or inhibition type reaction, a detection zone containing a binder which can bind with the ligand of the conjugate is formed on the porous membrane pad 16, and the binder can be the same substance with the target analyte in the sample or the similar derivatives of the target analyte. In the immunoassay, the signal intensity generated by the label of the conjugate is proportional or inversely proportional to the amount of the analyte in the sample. Thus, the existence of the analyte can be determined qualitatively, such as, positive or negative. Further, the amount of the analyte can be determined quantitatively by comparing the detected signal intensity with a standard signal intensity or with a standard colorimetry table.

Figure 6:
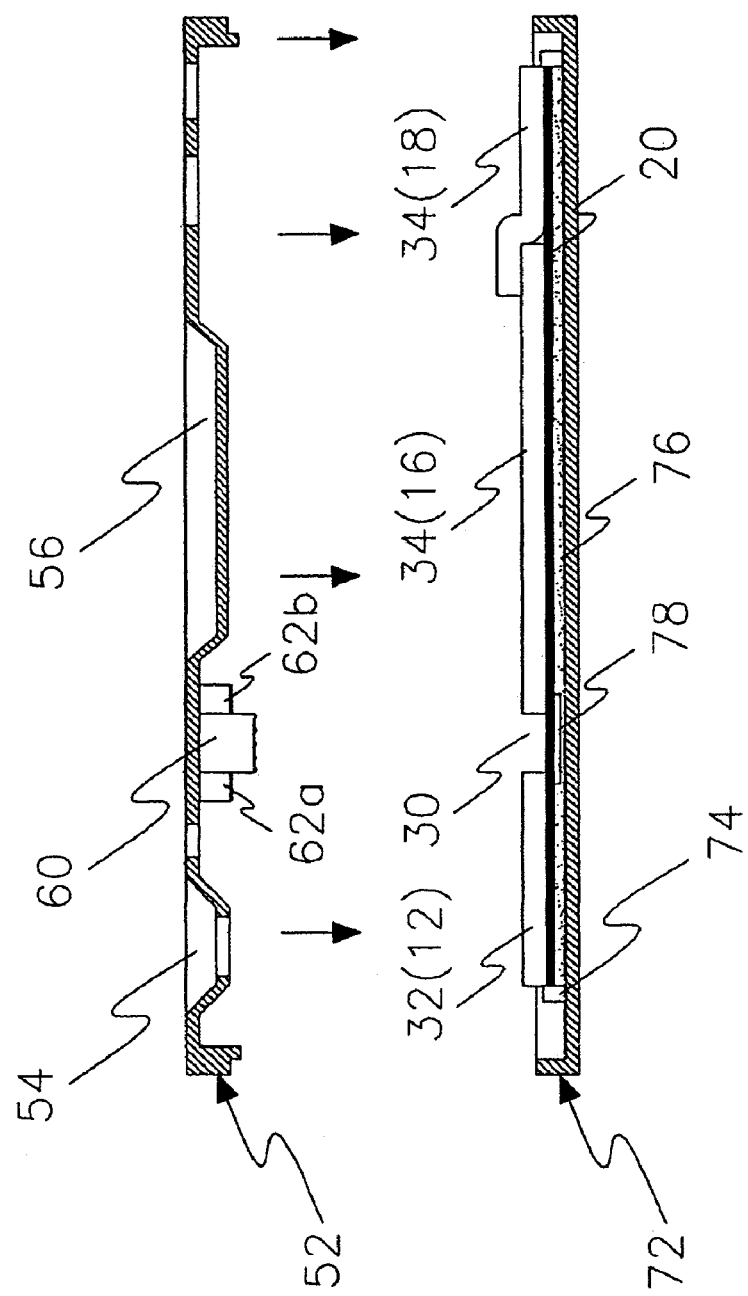
FIG. 6 is a side cross-sectional view of a non-continuous immunoassay device according to the third embodiment of the present invention.
Figure 7:
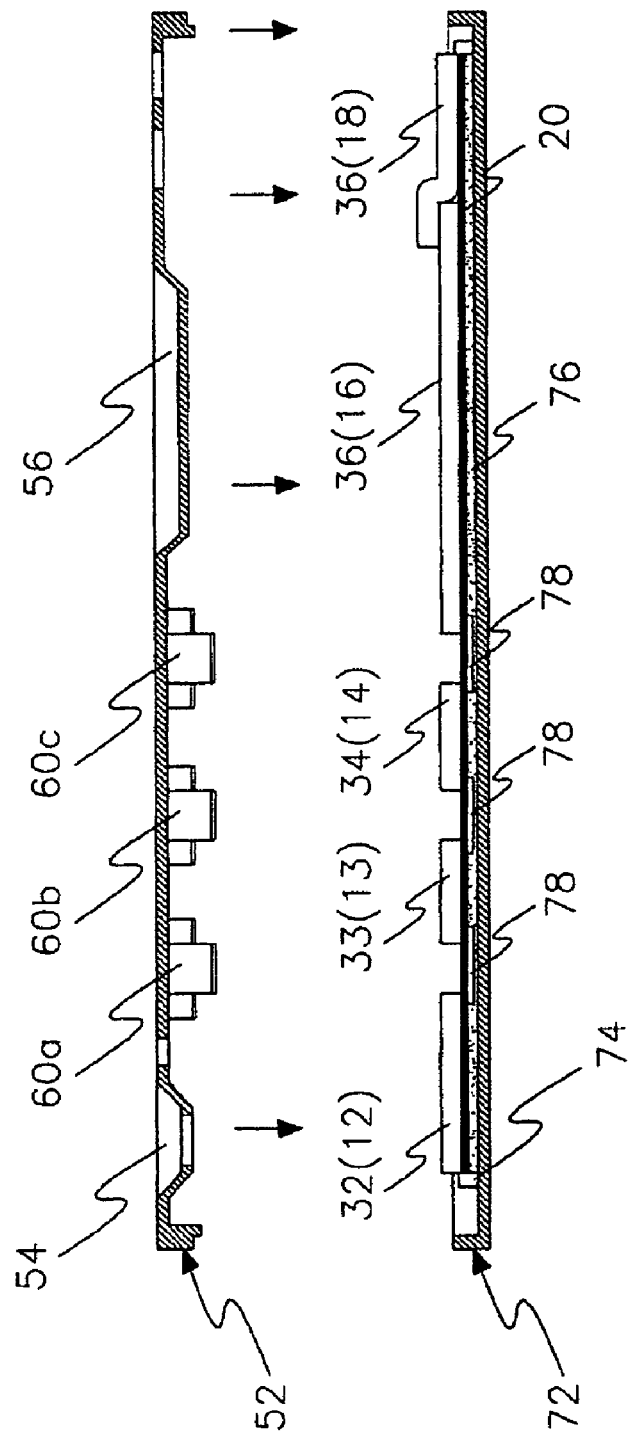
FIG. 7 is a modified example of a non-continuous immunoassay device according to the third embodiment of the present invention.

FIG. 6 is a side cross-sectional view of a non-continuous immunoassay device according to the third embodiment of the present invention, and FIG. 7 is a modified example of the non-continuous immunoassay device according to the third embodiment. The immunoassay device of the third embodiment has substantially same configuration with that of the first embodiment except that the immunoassay device includes the first pad area 32 and the second pad area 34 that are spatially isolated from each other by a predetermined distance, and are formed on single strip shaped plastic backing 20, and optionally a buffering groove 78 is formed on the lower case 72 or on the pad-supporting member 76 under the space 30 between the first pad area 32 and the second pad area 34 for regular migration of the liquid sample. Preferably, the width of the buffering groove 78 is larger than the distance between the first pad area 32 and the second pad area 34. Therefore, when the ends of the first pad area 32 and the second pad area 34 are compressed by the shoulder 62a, 62b of the connecting member 60, the compressed ends of the first pad area 32 and the second pad area 34 can be downwardly displaced due to the buffering groove 78, which facilitate the uniform migration of the liquid sample. In the immunoassay device shown in FIG. 6, the first pad area 32 can include a sample pad 12, and the second pad area 34 can include a porous membrane pad 16 and/or an absorbent pad 18 which may be overlapped at their connecting ends.

In addition, as shown in FIG. 7, a plurality of pads can be mounted on the single strip shaped plastic backing 20, and a plurality of pads is spatially isolated by at least two parts. In the immunoassay device shown in FIG. 7, the four separated pads, namely, the first pad area 32, the second pad area 33, the third pad area 34, and the fourth pad area 36 are mounted on the single strip shaped plastic backing 20, and four pad areas are connected by the three connecting members 60a, 60b, 60c. In FIG. 7, the first pad 32 area, the second pad area 33, the third pad area 34, and the fourth pad area 36 include a sample pad 12, an auxiliary pad 13, a conjugate pad 14, and an overlapped porous membrane pad 16 and absorbent pad 18, respectively. The auxiliary pad 13 can be optionally formed as already described.

Figure 8:
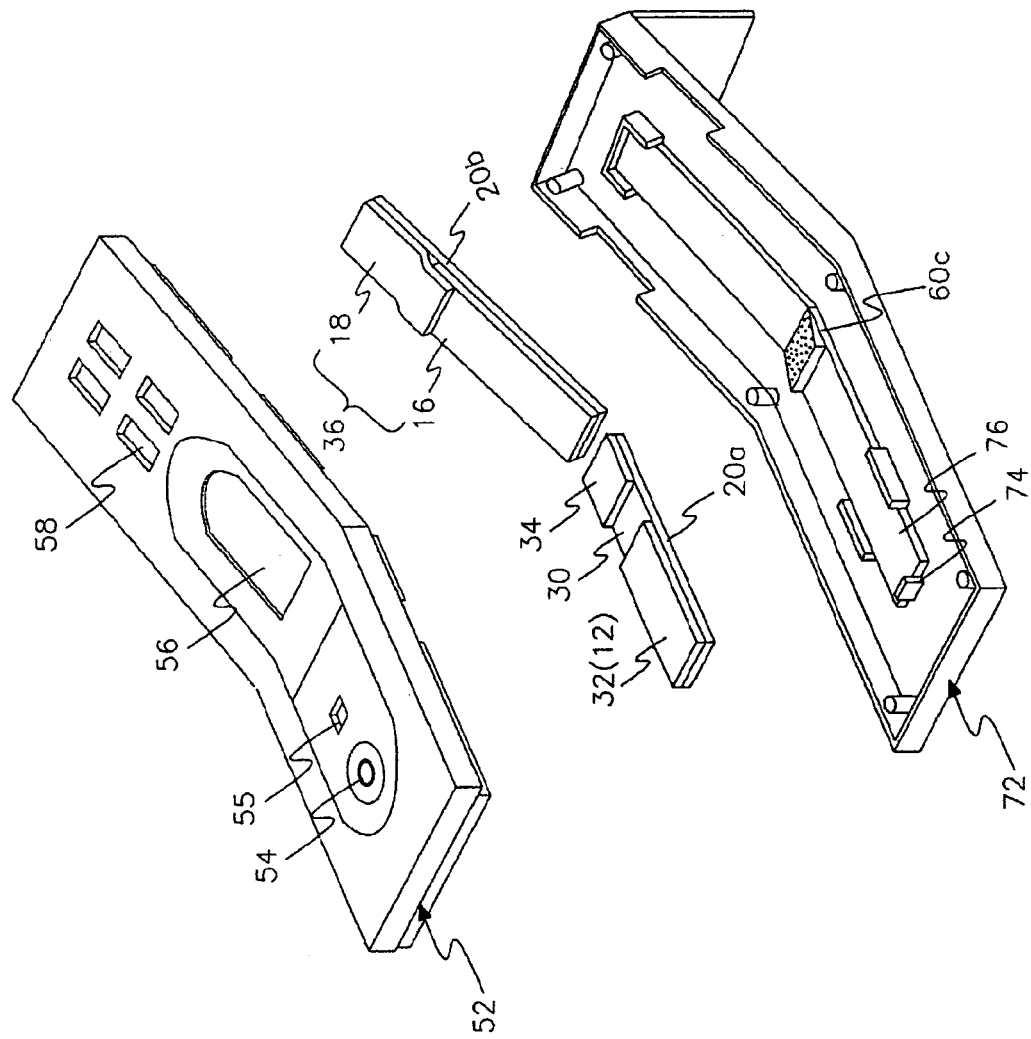
FIG. 8 is an exploded perspective view of a non-continuous immunoassay device according to the fourth embodiment of the present invention.
Figure 9:
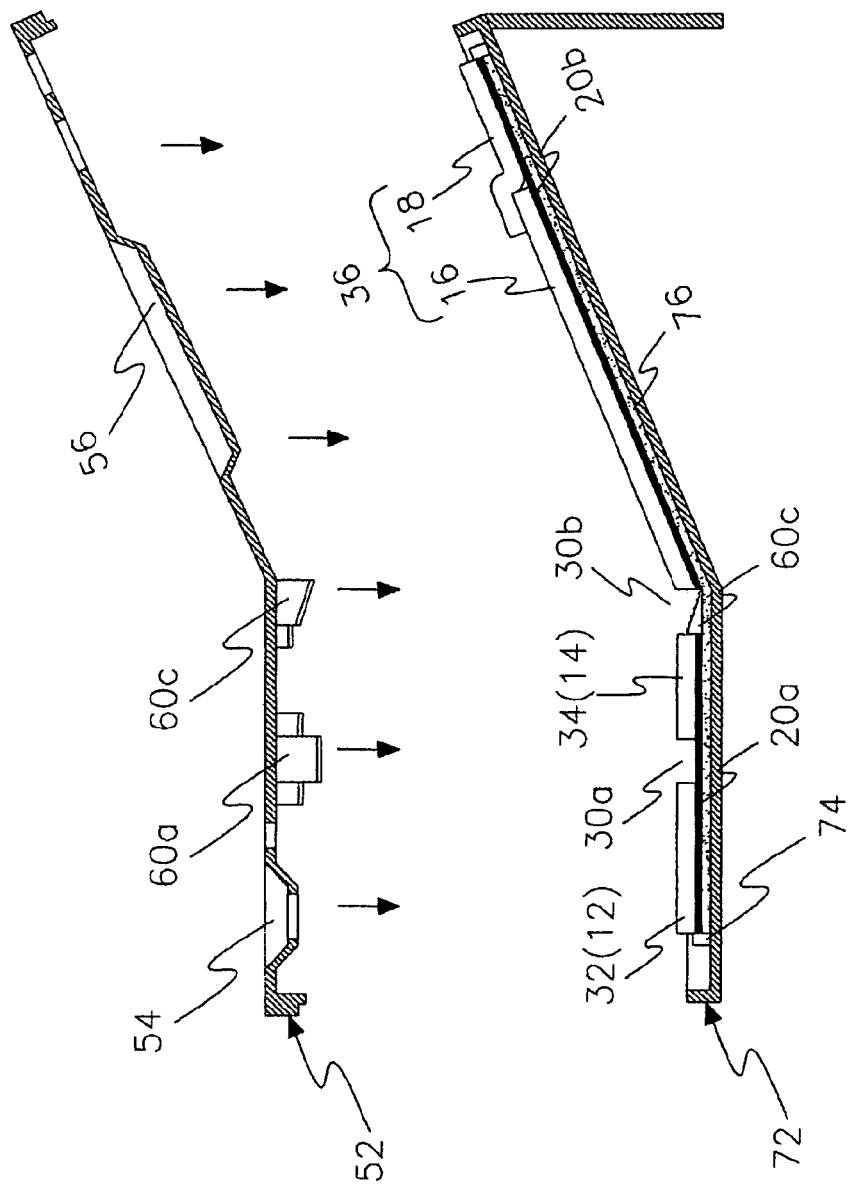
FIG. 9 is a side cross-sectional view of a non-continuous immunoassay device according to the fourth embodiment of the present invention.

FIG. 8 is an exploded perspective view of a non-continuous immunoassay device according to the fourth embodiment of the present invention, and FIG. 9 is a side cross-sectional view of the non-continuous immunoassay device. As shown in FIGS. 8 and 9, the immunoassay device in accordance with the fourth embodiment includes the three separated pads, namely, the first pad area 32, the second pad area 33, and the third pad area 34. Both the first pad area 32 and the second pad area 34 are formed on the first plastic backing 20a and the third pad area 36 is formed on the second plastic backing 20b. Since the first pad area 32, the second pad area 34, and the third pad area 36 are separated from each other, the shapes of the upper case 52 and the lower case 72 can be modified as occasion demands. The portions of the upper case and the lower case which cover the second pad area can be slanted with respect to the portions of the upper case and the lower case which cover the first pad by a predetermined angle. As shown in FIGS. 8 and 9, the portions of the upper case 52 and the lower case 72 which cover the first pad 32 area (including a sample pad 12) and the second pad area 34 (including a conjugate pad 14 or an auxiliary pad) are formed to be parallel to the ground, and the portions of the upper case 52 and the lower case 72 which cover the third pad area 36 (including a porous membrane pad 16 and an absorbent pad 18) are formed to be slanted with respect to the ground by a predetermined angle, for example 30 to 50 degree with respect to the ground. The bent configuration of the immunoassay device makes the user to easily observe the test result through the observation window 56.

Figure 11:
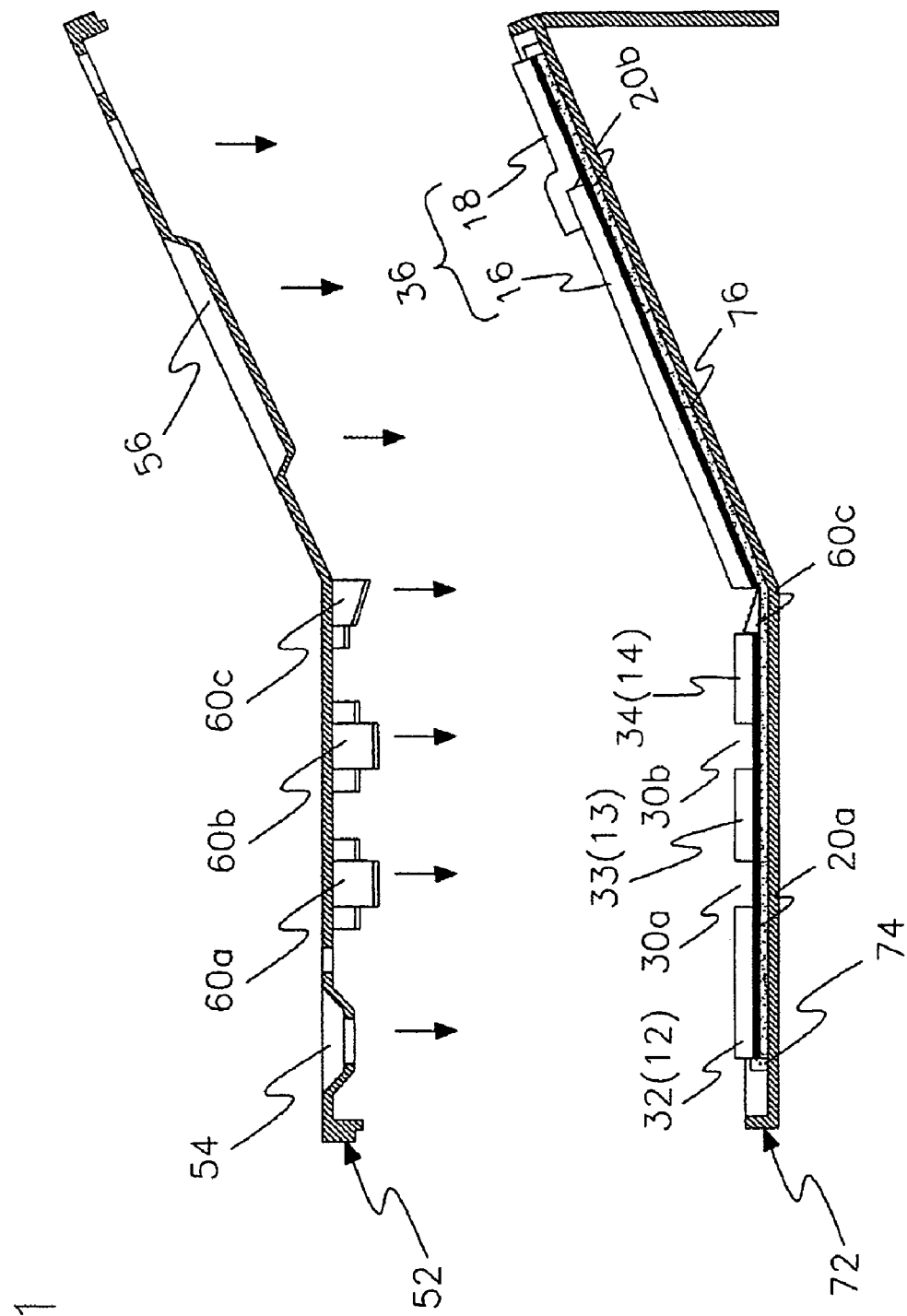
FIG. 11 is a modified example of a non-continuous immunoassay device according to the fourth embodiment of the present invention.

In this embodiment, the first connecting member 60a for connecting the first pad area 32 and the second pad area 34 has the same configuration with that of the first embodiment of the present invention. FIG. 10 shows a front view (A), a bottom view (B) and a side view (C) of the second connecting member 60c for connecting the second pad area 34 and the third pad 36 which is slanted by a predetermined angle. As shown in FIG. 10, the second connecting member 60c includes the first slanted protrusion 64a formed on the lower case 72 and the second slanted protrusion 64b formed on the upper case 52. The slanted surface of the second slanted protrusion 64b corresponds to the slanted surface of the first slanted protrusion 64a and a gap is formed between the two surfaces. Preferably, a shoulder 62a can be formed at one or more side of the second slanted protrusion 64b for compressing the end of the second pad area 34. The slanted surface of the first slanted protrusion 64a and the slanted surface of the second slanted protrusion 64b are separated by a predetermined distance (a gap distance) to form a capillary passage therebetween. Like the first embodiment of the present invention, it is preferable that the first and the second slanted protrusion 64a, 64b are tightly located at the space between the second pad area 34 and the third pad 36. It is also preferable that straight line shaped micro-protrusions 66 are formed on the shoulder 62a for tightly fixing the second pad area 34, and straight line shaped micro-protrusions 68 are formed on the slanted surfaces of the first and second slanted protrusions 64a, 64b for forming uniform capillary passage. If necessary, two or more pads can be formed on the first plastic backing 20a. As shown in FIG. 11, three separated pads 32, 33, 34 can be formed on the first plastic backing 20a, and the spaces 30a, 30b among the three pads 32, 33, 34 can be connected with two connecting member 60a, 60b. In the immunoassay device shown in FIG. 11, the three pads 32, 33, 34 can work as a sample pad 12, an auxiliary pad 13, and a conjugate pad 14, respectively.

Figure 12:
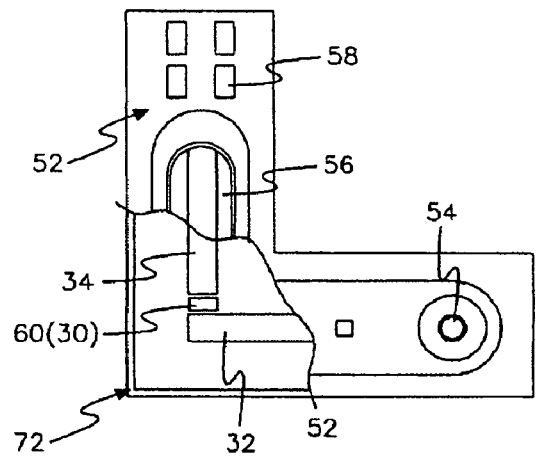
FIG. 12 is a partially cut-away top view of a non-continuous immunoassay device according to the fifth embodiment of the present invention.

FIG. 12 is a partially cut-away top view of a non-continuous immunoassay device according to the fifth embodiment of the present invention. The immunoassay device of the fifth embodiment has substantially same configuration with that of the first embodiment except that the first and the second pad areas are separated by a predetermined distance, and the first and the second pad areas 32, 34 are also separated by a predetermined angle. The two pads 32, 34 are positioned parallel to the ground, and the center point of the angle is the space 30 between the first and the second pad areas 32, 34, namely, the position of the connecting member 60. In the specific example shown in FIG. 12, the predetermined angle is 90 degree. The capillary passage exists in the space 30 between the first pad area 32 and the second pad area 34, and is formed by the connecting member 60 extending from the upper case 52. Therefore, a mobile phase such as liquid sample migrates from the first pad area 32 to the second pad area 34 through the capillary passage. As shown in the FIG. 12, the immunoassay device of the present invention has advantage that the configuration of the immunoassay device can be variously modified because pads 32, 34 are produced and positioned independently, and can be connected by a connecting member 60.

Figure 13:
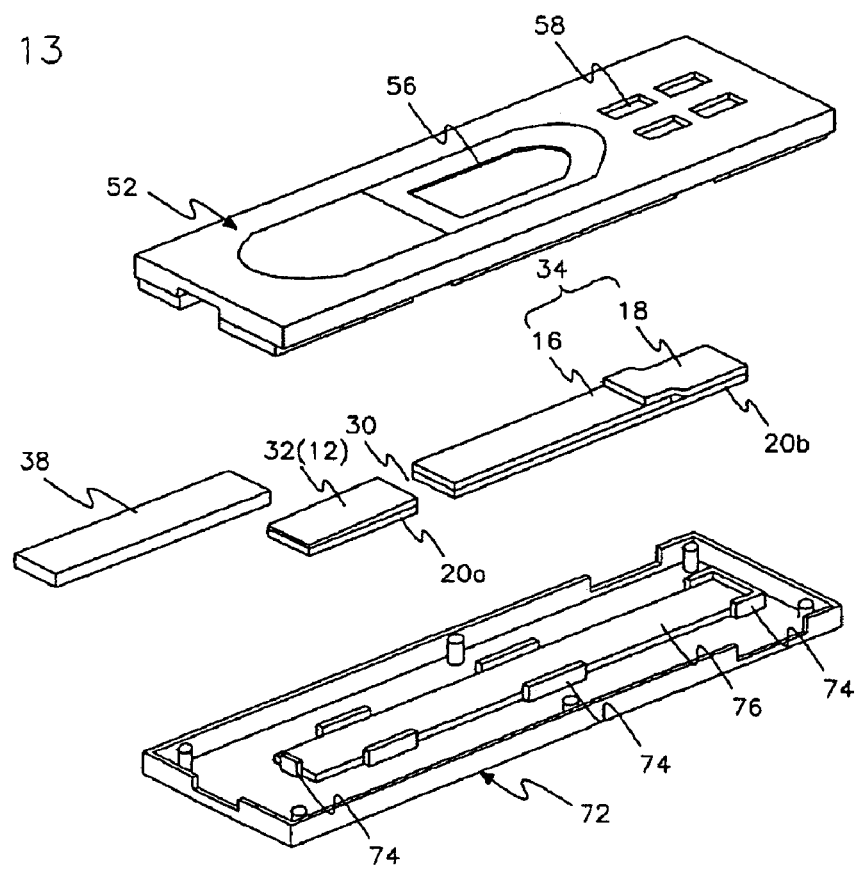
FIG. 13 is an exploded perspective view of a non-continuous immunoassay device according to the sixth embodiment of the present invention.

FIG. 13 is an exploded perspective view of a non-continuous immunoassay device according to the sixth embodiment of the present invention. The immunoassay device of the sixth embodiment has substantially same configuration with that of the first embodiment except that a wick 38 is installed through the end sides of the upper and/or lower case 52, 72 for communicating the first pad area 32 and out side of the device. In this embodiment, the first pad area 32 works as a sample pad 12, and a liquid sample in the outside of the device is introduced into the first pad area 32 through the wick 38. Therefore, the sample receiving hole needs not be formed on the upper case 52 in this embodiment. In this immunoassay device, the immunoassay by antigen-antibody reaction can be accomplished by immersing the wick 38 into a liquid sample. Then, the liquid sample is introduced into the first pad area 32 through the wick 38, and migrates to the second pad area 34 through a connecting member (now shown) which is formed between the first pad area 32 and the second pad area 34. The immunoassay device shown in FIG. 13 is capable of receiving a large amount of liquid sample, and needs not extra apparatus such as a syringe for applying a sample into the sample receiving hole.

Figure 14:
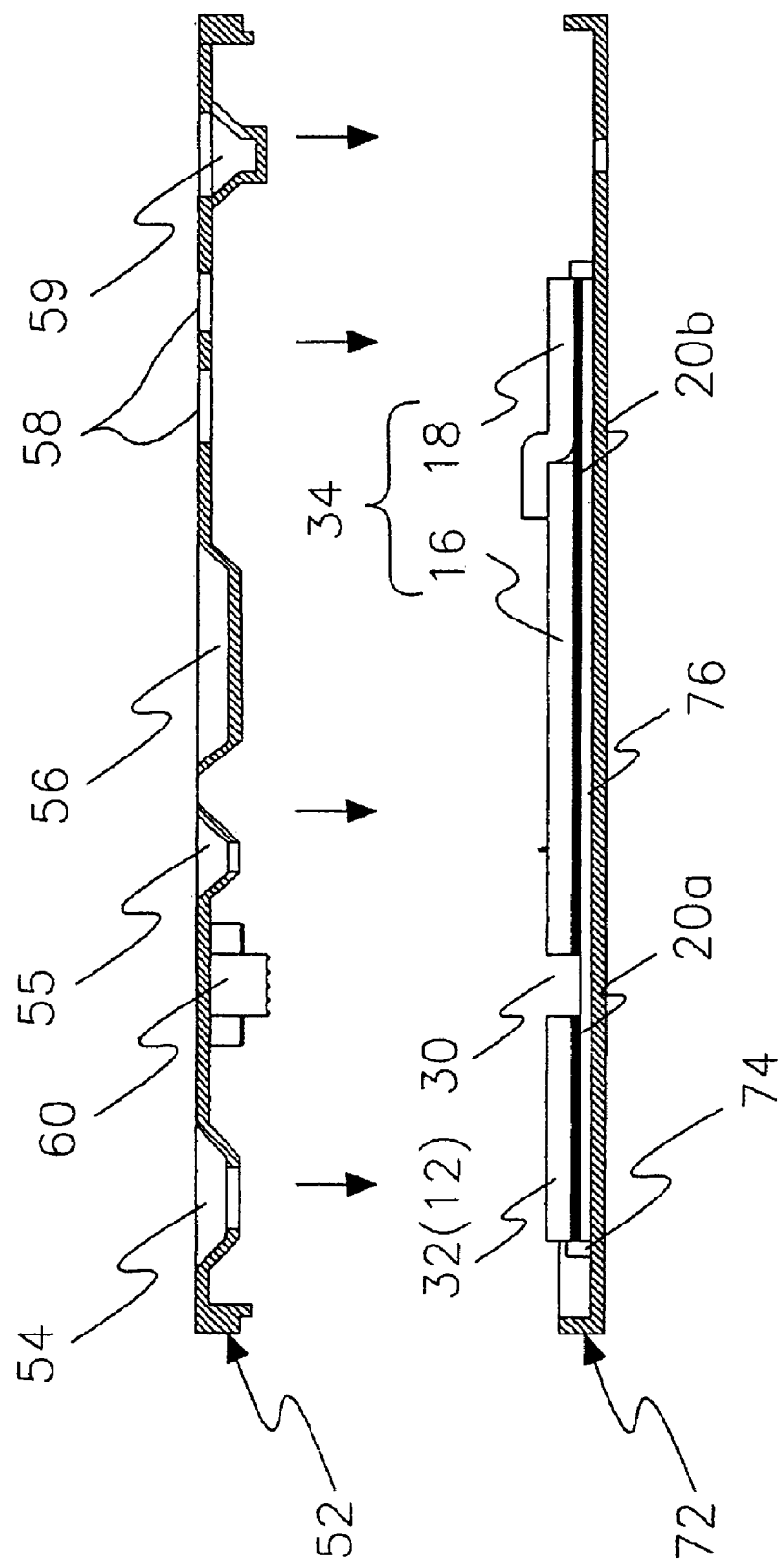
FIG. 14 is a side cross-sectional view of a non-continuous immunoassay device according to the seventh embodiment of the present invention.

FIG. 14 is a side cross-sectional view of a non-continuous immunoassay device according to the seventh embodiment of the present invention. The immunoassay device according to this embodiment is particularly useful for the immunoassay of whole blood sample. In the seventh embodiment and FIG. 14, the first pad area 32, the second pad area 34, the upper case 52, the lower case 72, the plurality of guides 74, the pad-supporting member 76, the plastic backings 20a, 20b, and the connecting member 60 have the same or similar functions as explained in the first embodiment of the present invention. In this embodiment, a liquid buffer is applied to the first pad area 32 as a mobile phase, and the applied liquid buffer migrates to the second pad area 34 through the gap between the connecting member 60 and the pad-supporting member 76 by a capillary action. Therefore, the connecting member 60 produces capillary passage (gap) for migrating the liquid buffer in the space 30 between the first pad area 32 and the second pad area 34.

As shown in FIG. 14, a buffer receiving part a1 for receiving the liquid buffer and a conjugate part a2 containing a conjugate are formed on the first pad area 32. The conjugate in the conjugate part a2 is mobilized by being dissolved with the buffer, and migrate with the liquid buffer. Therefore, the liquid buffer works as a mobile phase for dissolving and moving the conjugate, and, optionally, has the functions of diluting whole blood sample and/or inducing lysis of the whole blood components, such as erythrocyte. Conventional buffer solutions for an antigen-antibody reaction can be used in the present invention, and the liquid buffer can be selected according to the kind of the antigen-antibody reaction. Exemplary liquid buffer includes 10 mM to 1 M phosphate buffer. The first pad area 32 containing the conjugate can be made of a glass fiber, polyester, wood pulp paper, or the mixtures thereof. The sizes and locations of the buffer receiving part a1 and the conjugate part a2 can be adjusted according to the antigen-antibody reaction. The second pad area 34 includes a porous membrane pad 16, and a whole blood sample receiving part a3 for receiving whole blood sample, and a detection line a4 including a binder are formed on the porous membrane pad 16. The whole blood sample is a sample that are expected to contain a target analyte, and the binder can be an antigen or an antibody which can bind with the analyte in the sample and/or with the conjugate by an antigen-antibody reaction. If necessary, the second pad area 34 further includes an absorbent pad 18 for finally receiving the liquid buffer and the sample, and absorbent pad 18 can be overlapped with the porous membrane pad 16 at their connecting ends. The sizes and locations of the whole blood sample receiving part a3 and the detection line a4 or zone can be adjusted according to the antigen-antibody reaction.

Referring again to FIG. 14, a buffer receiving hole 54 is formed on the upper case 52 at the position corresponding to the buffer receiving part a1, and a sample receiving hole 55 is formed on the upper case 52 at the position corresponding to the whole blood sample receiving part a3 of the porous membrane pad 16. In addition, an observation window 56 is formed at the position corresponding to the detection line a4 or zone of the porous membrane pad 16, and an air ventilation hole 58 can be formed at the position corresponding to the absorbent pad 18. If necessary, a lysis hole 59 can be formed at the end portion of the upper case 52. The lysis hole 59 is provided for mixing the whole blood sample and a buffer for inducing lysis of the whole blood sample, for example, for inducing lysis of erythrocyte in the whole blood sample. The lysis hole 59 is useful when a hemolyzed whole blood sample is necessary for the immunoassay.

As shown in FIG. 14, when the buffer receiving hole 54 and the sample receiving hole 55 are formed separately, the whole blood sample cannot pass through the buffer receiving part a1 and the conjugate part a2. Therefore, when a hemolyzed whole blood sample is used, or when the whole blood sample is hemolyzed by the liquid buffer on the porous membrane pad 16, the whole blood components, such as the hemolyzed erythrocyte, pass through the porous membrane pad 16 having pores of relatively big sizes with relatively fast speed. Therefore, the background of the porous membrane pad 16 becomes clear at the time of detection of the test result, which makes the detection easier. In addition, when the whole blood sample is directly applied to the porous membrane pad 16, the reaction time for the antigen-antibody reaction increases, deviation of test result decreases, and the sensitivity and specificity in immunochromatographic assay can be improved.

In operation of the immunoassay device in accordance with the seventh embodiment of the present invention, the liquid buffer is applied into the buffer receiving part a1 to dissolve the conjugate contained in the conjugate part a2, and whole blood sample is applied into the whole blood sample receiving part a3 formed on the porous membrane pad 16. The order and interval of applying the liquid buffer and the whole blood sample can be appropriately controlled according to the kinds of the buffer, the analyte, and the conjugate, and the size and configuration of the immunoassay device. Then, the liquid buffer and the dissolved conjugate is moved through a capillary passage which is formed between the upper case 52 and the lower case 72 for covering the porous membrane pad 16 and the buffer receiving part a1, and formed by a protrusion 60 extending from at least one of the upper case 52 and the lower case 72, into the porous membrane pad 16. Then, the whole blood sample is mixed with the liquid buffer and the dissolved conjugate which are moved through the capillary passage. Then, the mixed sample reacts with the binder immobilized on the porous membrane pad 16 by an antigen-antibody reaction at the detection line a4, which can produce the color change of the detection line a4. By analyzing the color change of the detection line a4, immunoassay of the present invention can be performed.

Figure 15:
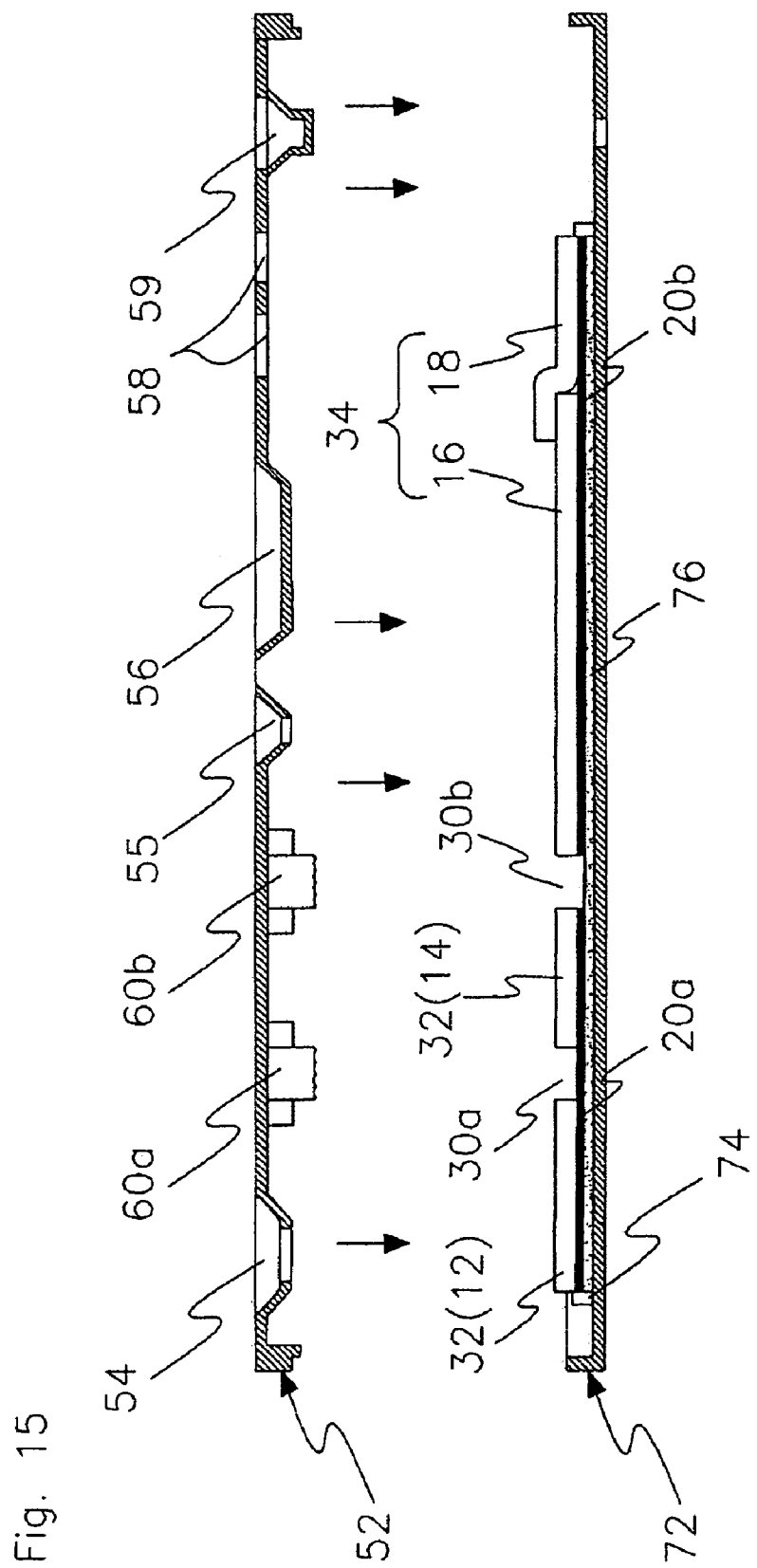
FIG. 15 is a side cross-sectional view of a non-continuous immunoassay device according to the eighth embodiment of the present invention.

FIG. 15 is a side cross-sectional view of a non-continuous immunoassay device according to the eighth embodiment of the present invention. The immunoassay device of this embodiment has substantially same configuration with that of the seventh embodiment except that (i) the first and the second pad areas 32, 34 are separately formed on the first and the second plastic backings 20a, 20b, respectively, (ii) the first pad area 32 includes a buffer pad 12 and a conjugate pad 14, which are separated by a predetermined distance, (iii) the first connecting member 60a is located at the space 30a between the buffer pad 12 and the conjugate pad 14, and the second connecting member 60b is located at the space 30b between the first pad area 32 and the second pad area 34. When two or more connecting members 60a, 60b are used, the migration rate of the mobile phase passing each pad can be controlled individually, which increases the sensitivity of immunoassay more effectively. In addition, when a pad is damaged, only the damaged pad can be exchanged instead of discarding whole pads. However, if necessary, the buffer pad 12 and the conjugate pad 14 can be overlapped at their connecting ends.

In operation of the eighth embodiment of the present invention, the whole blood sample is applied into the porous membrane pad 16 through the sample receiving hole 55 formed on the upper case 52, and the liquid buffer is applied into the buffer pad 12 through the buffer receiving hole 54 formed on the upper case 52. Then, the liquid buffer is moved into the conjugate pad 14 through the capillary passage which is formed between the upper case 52 and the lower case 72, and formed by the first connecting member 60a extending from the upper case 52, and mixed with the conjugate for desired time interval at the conjugate pad 14. The mixed buffer is moved again into the second pad area 34 through the capillary passage which is formed by the second connecting member 60b extending from the upper case 52. The gap distances of the capillary passages are adjusted according to the analyte in the sample, the liquid buffer, the conjugate, and the antigen-antibody reaction. For example, when the liquid buffer includes a chemical substance or a protein to reduce a non-specific antigen-antibody reaction, the first and the second connecting members 60a, 60b can be used to reduce the migration speeds of the liquid buffer and/or the conjugate so that the chemical substance or the protein react for enough time interval to reduce the non-specific antigen-antibody. Therefore, the first and the second connecting members 60a, 60b works as a reaction barrier inducing a flow delay of the mobile phase, or works as an antigen-antibody reaction rate controller. The liquid buffer and the conjugate that migrate to the porous membrane pad 16 are mixed with the whole blood sample directly applied to the porous membrane pad 16, react with a binder immobilized on the porous membrane pad 16, and generate a signal detectable by a naked eye or a sensor.

Figure 16:
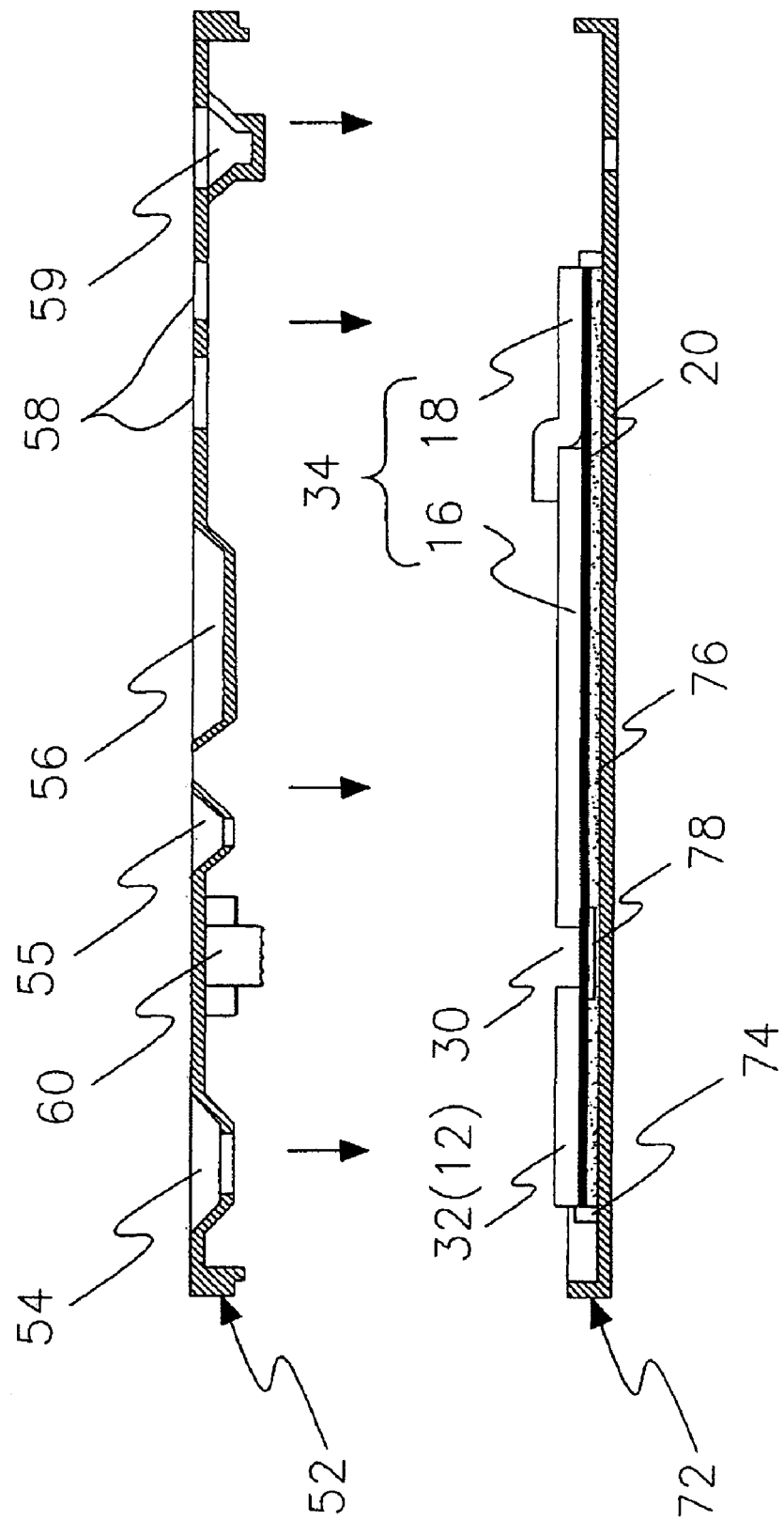
FIG. 16 is a side cross-sectional view of a non-continuous immunoassay device according to the ninth embodiment of the present invention.

FIG. 16 is a side cross-sectional view of a non-continuous immunoassay device according to the ninth embodiment of the present invention. The immunoassay device of the ninth embodiment has substantially same configuration with that of the seventh embodiment except that the immunoassay device includes the first pad area 32 and the second pad area 34 that are spatially isolated from each other by a predetermined distance, and are formed on single strip shaped plastic backing 20, and optionally a buffering groove 78 is formed on the lower case 72 or on the pad-supporting member 76 under the space 30 between the first pad area 32 and the second pad area 34 for regular migration of the liquid sample. Preferably, the width of the buffering groove 78 is larger than the distance between the first pad area 32 and the second pad area 34. Therefore, when the ends of the first pad 32 and the second pad area 34 are compressed by the shoulder of the connecting member 60, the compressed ends of the first pad 32 area and the second pad area 34 can be downwardly displaced due to the buffering groove 78, which facilitate the uniform migration of the liquid sample.

The immunoassay device of the present invention is useful for various rapid tests. Exemplary rapid test includes detections of pregnancy, ovulation, influenza virus, rotavirus, avian influenza, chlamydia and so on, in which the liquid sample is body fluids such as plasma, serum, urine, snivel, tear, and saliva, detection of using drug such as opium, morphine, philopon, heroin, amphetamine, cocaine, and cannabis, and detection of biochemical terror by analyzing the existence of cholera, SEB (staphylococcal enterotoxin B), botulinum, ricin, anthrax, brucella, and salmonella. Particularly, the immunoassay devices according to seventh to ninth embodiments of the present invention are useful for the detection of malaria, AIDS, hepatitis C, hepatitis B, syphilis, helicobacter pylori, tumor markers (AFP, PSA, CEA), tuberculosis, SARS, Dengue fever, leprosy, and so on, in which the liquid sample is whole blood. In this description, the "whole blood" represents blood components which include at least one component having a low migration speed on the conjugate pad as well as non-treated blood directly obtained from human or animal. Examples of the component having a low migration speed on the conjugate pad includes erythrocyte, blood plasma, blood serum and so on.

Hereinafter, the preferable experimental examples are provided for better understanding of the present invention. However, the present invention is not limited to the following experimental examples.

EXPERIMENTAL EXAMPLE 1

Test of Influenza Virus Using Immunoassay Device (A) Manufacture of nitrocellulose pad. The monoclonal antibodies against the nucleocapsid antigens of influenza virus type A and B were diluted with phosphate buffer solution, and the diluted antibodies were spread over a nitrocellulose pad (width: 25 mm, pore size: 10 to 12 μm to form test line 1 and 2, respectively. An anti-mouse immunoglobulin G antibody was obtained by immunizing a goat with a mouse immunoglobulin G, and the antibody was diluted with phosphate buffer solution. The diluted antibody was spread over the nitrocellulose pad to form a control line, and was dried in 37° C. Thermostat for immobilization. Then, phosphate buffer solution containing 0.05% by weight bovine serum albumin, 4% by weight % sucrose and 0.0625% by weight ionic surfactant was sprayed on the blank space of the nitrocellulose pad, and the pad was dried in 30° C. Thermostat for 60 to 120 minutes. The nitrocellulose pad was attached to a polypropylene backing plate on which an adhesive is coated, then an absorbent pad (obtained from Millipore Corp., U.S.A.) was also attached to the backing plate so that the absorbent pad and the nitrocellulose pad were overlapped by 1 mm.

(B) Manufacture of strip having sample pad and conjugate pad. The monoclonal antibodies against the nucleocapsid antigens of influenza virus type A and B were added to 1 ml of gold colloid-water solution to produce solutions of various antibody concentrations. Then, 150 mM sodium chloride solution, the amount of which was 1/10 of the volume of the gold colloid solution, was added to each gold colloid solution. The minimum amount of the gold colloid, which can stabilize the gold colloid solution, was determined from the above test. The antibody against the nucleocapsid antigen of influenza type A and B and the gold colloid were mixed by the determined ratio, and the mixture was treated with 1% by weight bovine serum albumin. The conjugate solution was centrifuged four times at 800 rpm, and the upper serum was removed. Then, 1% by weight bovine serum albumin phosphate buffer solution was added again to the solution so that the absorbance of the conjugate solution was 10. The obtained gold colloid-antibody conjugate solution was diluted with distilled water containing 0.5% by weight sucrose until its absorbance becomes 2, and the diluted solution was sprayed over a glass fiber pad with spray ratio of 10 l/25 mm$^2$. Then, the glass fiber pad coated with the gold colloid-antibody conjugate solution was rapidly frozen with liquid nitrogen, and was freeze-dried in a freeze dryer for 20 hours. Finally, the freeze-dried pad was cut into pieces of 0.7 mm×30 mm size. The obtained antibody-gold conjugate pad and a sample pad were attached on a polypropylene backing plate on which an adhesive is coated so that the two pads were separated by 1 mm.

(C) Manufacture of immunoassay device. The strips produced at step (A) and (B) were installed on a lower case with a separation distance of 2 mm. Then, an upper case having two connecting members for connecting the sample pad, the antibody-gold conjugate pad and the nitrocellulose pad was assembled with the lower case to produce the immunoassay device according to the fourth embodiment of the present invention (FIG. 8). The positive and the negative influenza virus type A and B samples were tested with the produced immunoassay device, and the test was carried out with good sensitivity.

EXPERIMENTAL EXAMPLE 2

Test of Syphilis Using Immunoassay Device

Except of using syphilis antigen produced by gene recombination instead of the monoclonal antibody against the nucleocapsid antigen of influenza virus, the nitrocellulose pad and the antigen-gold conjugate pad were manufactured by the same method of Experimental example 1. The nitrocellulose pad was attached to a polypropylene backing plate on which an adhesive is coated, then an absorbent pad (U.S.A., Millipore company) was also attached to the backing plate so that the absorbent pad and the nitrocellulose pad were overlapped by 1 mm. In addition, a sample pad for whole blood, an auxiliary pad and the antigen-gold conjugate pad were consecutively attached on a separate polypropylene backing plate on which an adhesive is coated so that the neighboring pads were separated by 1 mm, respectively. The two produced strips were installed on a lower case with a separation distance of 2 mm. Then, an upper case having three connecting members for connecting the sample pad, the auxiliary pad, the antigen-gold conjugate pad and the nitrocellulose pad was assembled with the lower case to produce the immunoassay device according to the fourth embodiment of the present invention (FIG. 8). The positive and the negative syphilis samples were tested with the produced immunoassay device, and the test was carried out with good sensitivity.

EXPERIMENTAL EXAMPLE 3

Test of HGC Using Immunoassay Device

Except of using the monoclonal antibody against the alpha HCG antigen instead of the monoclonal antibody against the nucleocapsid antigen of influenza virus, the nitrocellulose pad and the antibody-gold conjugate pad were manufactured by the same method of Experimental example 1. A sample pad, the antibody-gold conjugate pad, and the nitrocellulose pad were consecutively attached on a polypropylene backing plate on which an adhesive is coated so that the neighboring pads were separated by 1 mm, respectively. Then an absorbent pad (obtained from Millipore Corp., U.S.A.) was also attached to the backing plate so that the absorbent pad and the nitrocellulose pad were overlapped by 1 mm. The produced strip was installed on a lower case. Then, an upper case having two connecting members for connecting the sample pad, the antibody-gold conjugate pad and the nitrocellulose pad was assembled with the lower case to produce the immunoassay device according to the third embodiment of the present invention. The positive and the negative HGC samples were tested with the produced immunoassay device, and the test was carried out with good sensitivity.

EXPERIMENTAL EXAMPLE 4

Test of HIV Virus Using Immunoassay Device

Except of using gp41 and gp36 which are envelope antigens of HIV virus type 1 and type 2 diluted with carbonate buffer solution instead of the monoclonal antibody against the nucleocapsid antigen of influenza virus diluted with phosphate buffer solution, the nitrocellulose pad and the antigen-gold conjugate pad were manufactured by the same method of Experimental example 1. A sample pad for whole blood, the auxiliary pad, the antigen-gold conjugate pad, and the nitrocellulose pad were consecutively attached on a polypropylene backing plate on which an adhesive is coated so that the neighboring pads were separated by 1 mm, respectively. Then an absorbent pad (obtained from Millipore Corp., U.S.A.) was also attached to the backing plate so that the absorbent pad and the nitrocellulose pad were overlapped by 1 mm. The produced strip was installed on a lower case. Then, an upper case having three connecting members for connecting the sample pad, the auxiliary pad, the antigen-gold conjugate pad and the nitrocellulose pad was assembled with the lower case to produce the immunoassay device according to the third embodiment of the present invention (FIG. 7). The positive and the negative HIV virus type 1 and 2 samples were tested with the produced immunoassay device, and the test was carried out with good sensitivity.

EXPERIMENTAL EXAMPLE 5

Test of HGC Using Immunoassay Device

Except that a wick was mounted on the end of a sample pad, the immunoassay device was produced according to the method of Experimental example 3. The produced immunoassay device corresponds to the immunoassay device of the sixth embodiment of the present invention (FIG. 13). By applying a liquid sample through the wick, the positive and the negative HGC samples were tested, and the test was carried out with good sensitivity.

EXPERIMENTAL EXAMPLE 6

Test of Malaria Antigen and Antibody Using Whole Blood

Except of using the monoclonal antibodies against the malaria p.v/p.f antigen and malaria nucleocapsid antigen instead of the monoclonal antibodies against the nucleocapsid antigens of influenza virus, the nitrocellulose pad and the antibody-gold conjugate pad were manufactured by the same method of Experimental example 1. A buffer pad and the antibody-gold conjugate pad were consecutively attached on a polypropylene backing plate on which an adhesive is coated so that the two pads were separated by 1 mm. The produced nitrocellulose pad and the pad including the buffer pad and the antibody-gold conjugate pad were installed on a lower case so that the two pads were separated by 1 mm. Then, an upper case having two connecting members for connecting the buffer pad, the antibody-gold conjugate pad and the nitrocellulose pad was assembled with the lower case to produce the immunoassay device according to the eighth embodiment (FIG. 15) of the present invention. The positive and the negative malaria p.v/p.f antigen or malaria antibody samples were tested with the produced immunoassay device, and the test was carried out with good sensitivity. In this experiment, 100 mM phosphate buffer was used as the buffer, non-hemolyzed whole blood was used as the sample, and the non-hemolyzed whole blood was hemolyzed on the nitrocellulose pad by the buffer applied to the buffer pad.

As described in detail, the immunoassay device of the present invention is capable of controlling the migration speed of a mobile phase flowing through the pads for immunoassay, and thus controlling the antigen-antibody reaction time according to the kind of the antigen-antibody reaction. While the present invention has been shown and described with reference to certain preferred embodiments thereof, it will be understood by those skilled in the art that various changes in form and details may be made therein without departing from the spirit and scope of the invention as defined by the appended claims.

What is claimed is:

1. An immunoassay device, comprising:
   a first pad area including at least a sample pad for receiving a liquid sample;
   a second pad area which is spatially separated from the first pad area by a pre-determined distance, and to which the liquid sample migrates;
   an upper case for covering upper parts of the first pad area and the second pad area;
   a lower case for covering lower parts of the first pad area and the second pad area; and
   a connecting member which is a liquid non-permeable protrusion formed on and extending from at least one of the upper case and the lower case, and located between the first pad area and the second pad area to form a capillary passage for moving the liquid sample between the first pad area and the second pad area.

2. The immunoassay device according to claim 1, further comprising a pad-supporting member formed on the lower case for supporting the first and the second pad areas.

3. The immunoassay device according to claim 1, wherein the connecting member includes two shoulders, one of the two shoulders fixing an end of a pad in the first pad area and the other one of the two shoulders fixing an end of a pad in the second pad area.

4. The immunoassay device according to claim 1, wherein a plurality of micro-protrusions is formed on the liquid non-permeable protrusion forming a capillary passage.

5. The immunoassay device according to claim 1, wherein the connecting member is treated with hydrophobic or hydrophilic material to control migration speed of the liquid sample.

6. The immunoassay device according to claim 5, wherein the connecting member is treated by coating the connecting member with hydrophobic or hydrophilic latex particles or compounds, or by adhering hydrophobic or hydrophilic group on the connecting member by using a plasma.

7. The immunoassay device according to claim 1, wherein the first pad area includes a sample pad, and the second pad area includes a porous membrane pad and an absorbent pad which are overlapped at connecting ends thereof.

8. The immunoassay device according to claim 1, wherein the first pad area and the second pad area are formed each on a separate plastic backing.

9. The immunoassay device according to claim 1, wherein the first pad area includes a sample pad and a conjugate pad, which are formed on a first plastic backing and are separated by a predetermined distance, and the second pad area includes a porous membrane pad and an absorbent pad which are formed on the second plastic backing.

10. The immunoassay device according to claim 1, wherein the portions of the upper case and the lower case which cover the second pad area slanted with respect to the portions of the upper case and the lower case which cover the first pad area by a predetermined angle.

11. The immunoassay device according to claim 1, wherein the first pad area and the second pad area are separated by a predetermined angle with respect to the connecting member.

12. An immunoassay device, comprising:
   a strip shaped plastic backing;
   two or more pads for immunoassay that are formed on the plastic backing and spatially separated from each other by a predetermined distance;
   an upper case for covering the upper parts of the two or more pads;
   a lower case for covering a lower part of the plastic backing; and
   at least one connecting member which is a liquid non-permeable protrusion formed on and extending from at least one of the upper case and the lower case, and located between the pads to form a capillary passage for moving a liquid sample between the two pads.

13. The immunoassay device according to claim 12, wherein the two or more pads for immunoassay includes a sample pad, a conjugate pad and a porous membrane pad on which a detection zone is formed.

* * * * *